United States Patent
Scalone et al.

(10) Patent No.: US 6,777,559 B2
(45) Date of Patent: Aug. 17, 2004

(54) PROCESS FOR PREPARING HETEROCYCLIC INDENE ANALOGS

(75) Inventors: Michelangelo Scalone, Birsfelden (CH); Thomas Albert Zeibig, Mutterstadt (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/054,462

(22) Filed: Jan. 22, 2002

(65) Prior Publication Data
US 2002/0099223 A1 Jul. 25, 2002

(30) Foreign Application Priority Data
Jan. 25, 2001 (EP) ............................................. 01101584

(51) Int. Cl.[7] ................... C07D 207/36; C07D 207/48; C07D 207/50
(52) U.S. Cl. ........................ 548/484; 548/439; 548/440; 548/441; 548/444; 548/508; 548/562; 549/52; 549/466; 549/430; 568/13; 568/17; 556/143
(58) Field of Search ................................. 548/508, 439, 548/440, 441, 484, 443

(56) References Cited

U.S. PATENT DOCUMENTS 6,291,685 B1    9/2001  Junghans et al.

FOREIGN PATENT DOCUMENTS

EP    1 078 923    7/2000

OTHER PUBLICATIONS

Hiday, et al., Advances in Metal–Organic Chemistry, vol. 4, pp. 275–309, 1995.

Masakazu Iwasaki et al., Journal of Organic Chemistry, vol. 56, 1991, pp. 1922–1927.

*Primary Examiner*—Ceila Chang
*Assistant Examiner*—Rebecca Anderson
(74) *Attorney, Agent, or Firm*—George W. Johnston; John P. Parise

(57) ABSTRACT

A process for the preparation heterocyclic indene analogs, especially with the preparation of 4-hydroxycarbazole or N-protected 4-hydroxycarbazole, involves cyclocarbonylation followed by saponification. This process avoids high temperatures and high catalyst loadings.

30 Claims, No Drawings

PROCESS FOR PREPARING HETEROCYCLIC INDENE ANALOGS

BACKGROUND OF THE INVENTION

1. Field

The present invention is concerned with a novel process for the preparation of heterocyclic indene analogs, especially with the preparation of 4-hydroxycarbazole or N-protected 4-hydroxycarbazole. These compounds may be used as a building block for pharmaceutically active compounds, e.g. 1-(9H-carbazol-4-yloxy)-3-[[2-(2methoxy-phenoxy)ethyl]amino]-2-propanol (carvedilol). This compound is known in the art and is described for example in EP 0 004920. It is especially useful for prophylaxis and treatment of heart- and circulatory diseases like, for example, hypertension, coronary heart failure, angina pectoris and the like.

2. Description

Processes for the catalytic cyclocarbonylation of pyrrole and indole derivatives have been described by Hiday et al., Advances in Metal-Organic Chemistry, Volume 4, 275–309. These processes are characterized by high temperatures, high catalyst loadings and modest selectivity. Moreover, the educts necessary for the reactions in these processes are expensive, since they have to be prepared by lengthy procedures, and are not available commercially.

Surprisingly, it has been found that using the process according to the present invention, heterocyclic indene analogs, e.g. indole or carbazole derivatives (such as 4-hydroxycarbazole and N-protected 4-hydroxycarbazole) can be prepared from commercial educts and without the aforementioned disadvantages.

SUMMARY OF THE INVENTION

The subject invention provides a process preparing a compound of the formula:

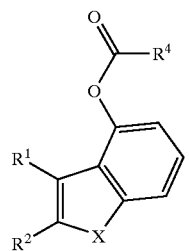

(III)

wherein
- $R^1$ and $R^2$ are independently selected from the group consisting of hydrogen and lower-alkyl; or
- $R^1$ and $R^2$ together with the ring carbon atoms to which they are attached form a monovalent carbocyclic or a monovalent carbocyclic aromatic ring or a monovalent carbocyclic or monovalent carbocyclic aromatic ring may substituted by halogen, lower-alkyl or lower-alkoxy;
- X is O, S or N—Z;
- Z is an amino protecting group selected from the group consisting of $SO_2R^a$, $NMe_2$, $CO_2R^b$ and $CON(R^c)_2$;
- $R^a$ is lower-alkyl or aryl; and
- $R^b$ and $R^c$ are lower-alkyl.

This process comprises:
cyclocarbonylating a compound of formula:

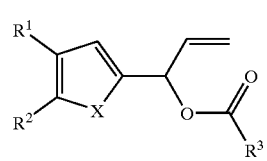

(II)

wherein $R^3$ is lower-alkyl, aryl or aralkyl, and $R^1$, $R^2$ and X are as defined above;

to form a compound of formula:

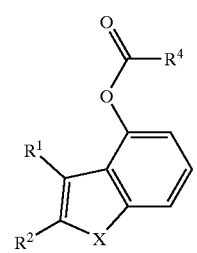

(III)

wherein $R^4$ is lower-alkyl or aryl and $R^1$, $R^2$ and X are as defined above; and saponifying the compound of formula (III) to produce the compound of formula (I).

It is favored where X is N—Z or Z is $SO_2R^a$ and $R^a$ is phenyl. It is also favored where $R^1$ and $R^2$ together with the ring carbon atoms to which they are attached form a phenyl ring. Another favored embodiment is where $R^3$ is methyl or phenyl.

Beneficially, the cyclocarbonylating is carried out in the presence of a base, an anhydride, and a catalyst comprising a transition metal compound and a ligand. Preferred transition metal compounds are palladium salts, such as Pd(OAc)$_2$, Pd$_2$dba$_3$, PdCl$_2$, Pd$_2$Cl$_2$($\pi$-allyl)$_2$, PdCl$_2$(NCMe)$_2$, [Pd(NCMe)$_4$](BF$_4$)$_2$ or Pd/C. Pd(OAc)$_2$ is favored.

The ligand can be $P(R^5)(R^6)(R^7)$ or $(R^5)(R^6)P$—(Y)—$P(R^5)(R^6)$ wherein $R^5$, $R^6$ and $R^7$ each independently are $C_{1-8}$-alkyl, cyclohexyl, benzyl, naphthyl, 2- or 3-pyrrolyl, 2- or 3-furyl, 2- or 3-thiophenyl, 2- or 3- or 4-pyridyl, phenyl or phenyl which is substituted by $C_{1-4}$-alkyl, $C_{1-4}$-alkoxy, halogen, trifluoromethyl, lower alkylydenedioxy or phenyl and Y is binaphthyl, 6,6'-dimethyl- or 6,6'-dimethoxybiphenyl-2,2'-diyl, or one of the groups —(CH$_2$)$_n$—, —CH$_2$CH$_2$—P(C$_6$H$_5$)—CH$_2$CH$_2$—,

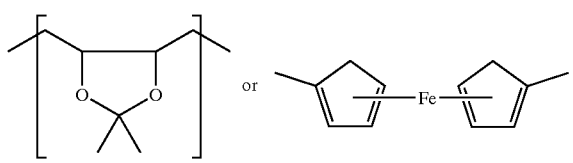

(IV)

and n is a number of 1–8. A preferred ligand is selected from the group consisting of triphenylphosphine, and

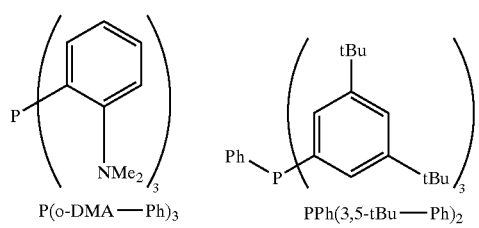

P(o-DMA—Ph)₃   PPh(3,5-tBu—Ph)₂

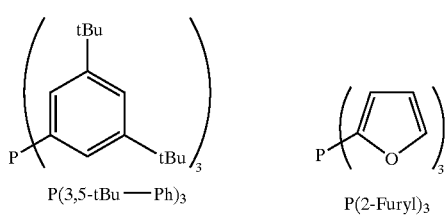

P(3,5-tBu—Ph)₃   P(2-Furyl)₃

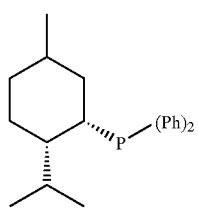
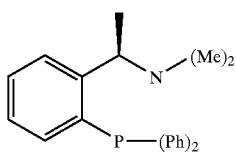

NMDPP   AMPHOS

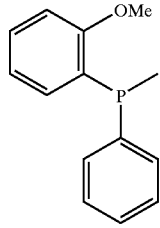

DIOP   PAMP

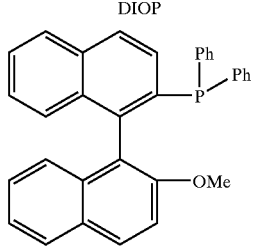

MOP   (S,S)-DDPPI

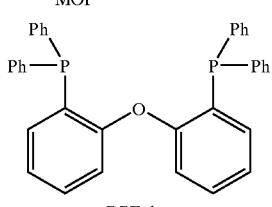
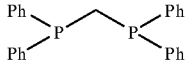

DPEphos   DPPM

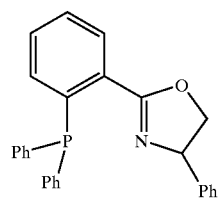
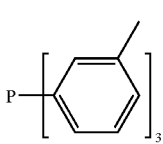

TPP-ox-Ph   P(m-Tol)₃

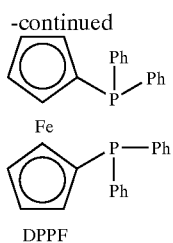

DPPF

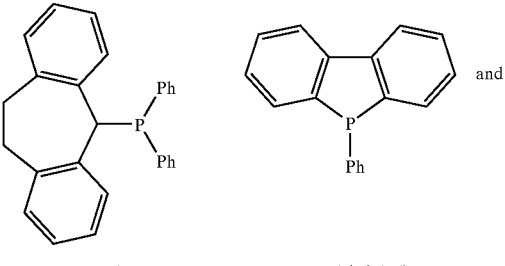

TROPP-Ph   PPh(Diphol)

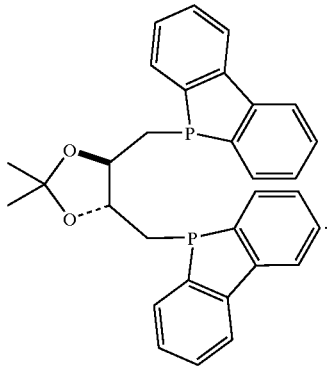

Diphol-DIOP

More favored is triphenylphosphine,

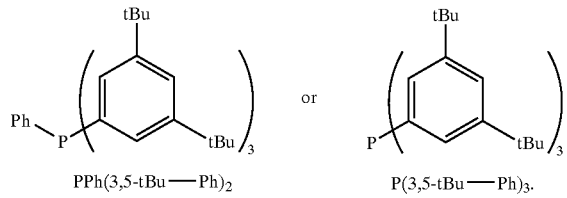 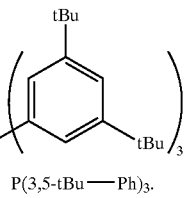

PPh(3,5-tBu—Ph)₂   or   P(3,5-tBu—Ph)₃.

The cyclocarbonylating can be carried out in the presence of a base selected from the group consisting of tri-alkyl-amines, di-alkyl-aryl-amines, pyridines, alkyl-N-piperidines, sodium hydroxide, potassium hydroxide or salts of carbonic acids. Presently, triethylamine is favored.

Anhydrides such as $(R^4(C=O))_2O$, wherein $R^4$ is as defined above are preferred. Favored anhydrides include acetic anhydride, propionic anhydride, butyric anhydride, isobutyric anhydride, pivalic anhydride, and benzoic anhydride.

Saponifying is can be performed in a biphasic mixture of sodium hydroxide in toluene or in a homogeneous mixture of sodium methylate in methanol.

A more favored process is where the cyclocarbonylating is carried out in the presence of a base selected from the group consisting of tri-alkyl-amines, di-alkyl-aryl-amines, pyridines, alkyl-N-piperidines, sodium hydroxide, potassium hydroxide and salts of carbonic acids. An anhydride of the formula $(R^4(C=O))_2O$, wherein $R^4$ is as defined as above is used. In addition, a catalyst comprising a transition metal compound and a ligand is provided. The transition metal compound is selected from the group consisting of Pd(OAc)$_2$, Pd$_2$dba$_3$, PdCl$_2$, Pd$_2$Cl$_2$($\pi$-allyl)$_2$, PdCl$_2$(NCMe)$_2$, [Pd(NCMe)$_4$](BF$_4$)$_2$, and Pd/C. The ligand is selected from the group consisting of P(R$^5$)(R$^6$)(R$^7$) and (R$^5$)(R$^6$)P—(Y)—P(R$^5$)(R$^6$) wherein R$^5$, R$^6$ and R$^7$ each independently are C$_{1-8}$-alkyl, cyclohexyl, benzyl, naphthyl, 2- or 3-pyrrolyl, 2- or 3-furyl, 2- or 3-thiophenyl, 2- or 3- or 4-pyridyl, phenyl or phenyl which is substituted by C$_{1-4}$-alkyl, C$_{1-4}$-alkoxy, halogen, trifluoromethyl, lower alkylydenedioxy or phenyl and Y is binaphthyl, 6,6'-dimethyl- or 6,6'-dimethoxybiphenyl-2,2'-diyl, or one of the groups —(CH$_2$)$_n$—, —CH$_2$CH$_2$—P(C$_6$H$_5$)—CH$_2$CH$_2$—,

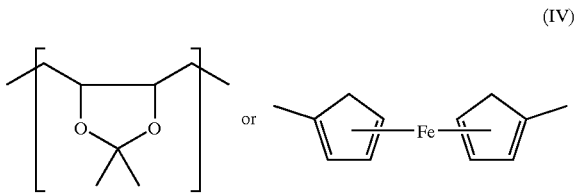

(IV)

and n is a number of 1–8.

All combinations of the above bases, anhydrides, and catalysts are envisioned, as are the choices of ligands, transition metal compounds and saponifying agents.

The subject invention also provides a compound of formula:

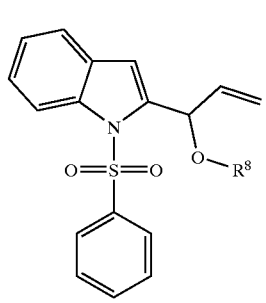

(IIa)

wherein R$^8$ is hydrogen, acetyl or benzoyl.

DETAILED DESCRIPTION OF THE PREFERRED EMBODIMENTS

The present invention will now be described in terms of its preferred embodiments. These embodiments are set forth to aid in understanding the invention but are not to be construed as limiting.

The present invention refers to a process for the preparation of heterocyclic indene analogs of formula (I)

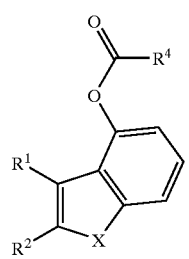

(III)

wherein
R$^1$ and R$^2$ are independently selected from hydrogen or lower-alkyl; or R$^1$ and R$^2$ together with the ring carbon atoms to which they are attached form a monovalent carbocyclic or a phenyl ring, wherein the said monovalent carbocyclic or phenyl ring may optionally be substituted by halogen, lower-alkyl or lower-alkoxy;

X is O, S or N—Z;

Z is an amino protecting group selected from SO$_2$R$^a$, NMe$_2$, CO$_2$R$^b$ and CON(R$^c$)$_2$; and R$^a$ is lower-alkyl or aryl;

R$^b$ and R$^c$ are lower-alkyl;

said process comprising cyclocarbonylation of a compound of formula (II)

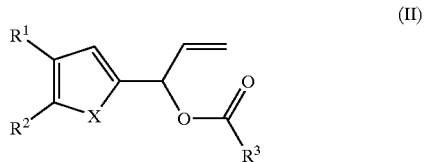

(II)

wherein R$^3$ is lower-alkyl, aryl or aralkyl and R$^1$, R$^2$ and X are as defined above;

to produce a compound of formula (III)

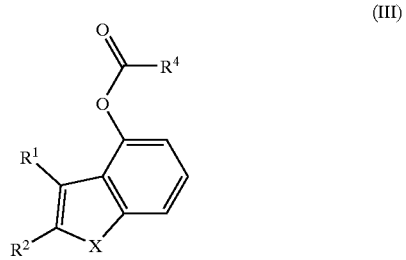

(III)

wherein R$^4$ is lower-alkyl or aryl and R$^1$, R$^2$ and X are as defined above;

followed by saponification.

This process provides an efficient cyclocarbonylation reaction under mild conditions. In addition, substrates for the cyclocarbonylation reaction (compound of formula (II)) do not need to be purified, e.g. by crystallization or distillation, but can be used as "crude" material.

According to the present invention, the term "cyclocarbonylation" refers to an introduction of a carbonyl group coupled to the formation of an aromatic cyclic ring structure.

The term "transition metal compound" refers to a metal-phosphine complex compound wherein the term metal refers to Pd, Pt, Ru, Co, Rh or Ni, preferably Pd.

The term "ligand" refers to phosphine, arsine or stibine derivatives, preferable phosphine derivatives, of general formulae P(R$^5$)(R$^6$)(R$^7$), (R$^5$)(R$^6$)P—(X)—P(R$^5$)(R$^6$), As(R$^5$)(R$^6$)(R$^7$) or Sb(R$^5$)(R$^6$)(R$^7$), preferably P(R$^5$)(R$^6$)(R$^7$), wherein R$^5$, R$^6$, and R$^7$ are defined below.

The term "alkyl" refers to a branched or straight chain monovalent alkyl radical of one to nine carbon atoms (unless otherwise indicated). The term "lower-alkyl" refers to a branched or straight chain monovalent alkyl radical of one to four carbon atoms. This term is further exemplified by such radicals as methyl, ethyl, n-propyl, isopropyl, i-butyl, n-butyl, t-butyl and the like.

The term "alkoxy", alone or in combination, signifies a group of the formula alkyl-O— in which the term "alkyl" has the significance given above. Examples of such "alkoxy" radicals are methoxy, ethoxy, n-propoxy, isopropoxy, n-butoxy, isobutoxy, sec.butoxy and tert.butoxy, preferably methoxy and ethoxy.

The term "aryl" refers to a monovalent carbocyclic aromatic radical, e.g. phenyl or naphthyl, optionally substituted, independently, with halogen, lower-alkyl, lower-alkoxy, lower-alkylenedioxy, carboxy, trifluoromethyl and the like.

The term "aralkyl" refers to a residue —CH$_2$-aryl wherein the term aryl is as defined above.

The term "alkylenedioxy" refers to C$_{1-3}$-alkyl-dioxy groups, such as methylenedioxy, ethylenedioxy or propylenedioxy.

The term "halogen" refers to fluorine, chlorine, and bromine.

In more detail, the present invention refers to a process for the preparation of compounds of formula (I)

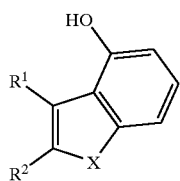

(I)

wherein
R$^1$ and R$^2$ are independently selected from hydrogen or lower-alkyl; or
R$^1$ and R$^2$ together with the ring carbon atoms to which they are attached form a monovalent carbocyclic or phenyl ring, wherein the said monovalent carbocyclic or phenyl ring may optionally be substituted by halogen, lower-alkyl or lower-alkoxy;
X is O, S or N—Z;
Z is an amino protecting group selected from SO$_2$R$^a$, NMe$_2$, CO$_2$R$^b$ and CON(R$^c$)$_2$; and
R$^a$ is lower-alkyl or aryl;
R$^b$ and R$^c$ are lower-alkyl;
said process comprising cyclocarbonylation of a compound of formula (II)

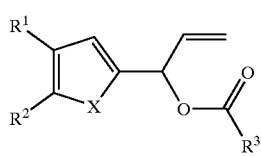

(II)

wherein R$^3$ is lower-alkyl, aryl or aralkyl and R$^1$, R$^2$ and X are as defined above;
to produce a compound of formula (III)

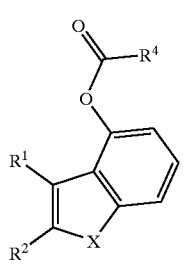

(III)

wherein R$^4$ is lower-alkyl or aryl and R$^1$, R$^2$ and X are as defined above;
followed by saponification.

Examples of lower-alkyl residues R$^1$ and R$^2$ are methyl, ethyl, n-propyl and isopropyl, with methyl being preferred. Preferred monovalent carbocyclic rings formed by substituents R$^1$ and R$^2$ together with the ring carbon atoms to which they are attached are cyclopentenyl, cyclohexenyl and cycloheptenyl, preferably cyclohexenyl. Such rings may be substitued by lower-alkyl, such as methyl and ethyl. The most preferable monovalent carbocyclic ring formed by substituents R$^1$ and R$^2$ together with the ring carbon atoms to which they are attached is unsubstituted cyclohexenyl. A phenyl residue formed by R$^1$ and R$^2$ together with the ring carbon atoms to which they are attached may be substituted by halogen, lower-alkyl or lower-alkoxy, preferably by chloro, bromo, methyl or methoxy. Most preferably, R$^1$ and R$^2$ together with the ring carbon atoms to which they are attached form an unsubstituted phenyl ring.

Examples of aryl residues in substituent R$^3$ are phenyl and phenyl substituted by halogen or lower alkyl, preferably unsubstituted phenyl. Preferable aralkyl residue R$^3$ is benzyl, optionally substituted by halogen or lower alkyl. Most preferable aralkyl residue R$^3$ is unsubstituted benzyl. Examples of lower-alkyl residues R$^3$ are methyl, ethyl, n-propyl, isopropyl and t-butyl, with methyl being preferred.

R$^4$ depends on the anhydride used in the cyclocarbonylation reaction. Examples of lower-alkyl residues are methyl, ethyl, n-propyl, isopropyl and t-butyl, with methyl being preferred. An example of aryl residues is phenyl. Such phenyl residue may be substituted by halogen, lower-alkyl or lower-alkoxy, preferably by chloro, bromo, methyl or methoxy. The most preferable aryl residue R$^4$ is unsubstituted phenyl.

Examples of lower-alkyl residues R$^a$, R$^b$ and R$^c$ are methyl, ethyl, n-propyl, isopropyl and t-butyl, with methyl being preferred. Examples of aryl residues R$^a$ are phenyl and naphthyl. Such rings may be substituted by halogen or lower-alkyl, preferably by chloro, methyl, ethyl or isopropyl. More preferably, aryl residue R$^a$ is phenyl, substituted by halogen or lower-alkyl, preferably by chloro, methyl, ethyl or isopropyl. Most preferred aryl residue R$^a$ is phenyl.

In another preferred embodiment, the present invention relates to a cyclocarbonylation process as described above, wherein R$^1$ and R$^2$ together with the ring carbon atoms to which they are attached form a phenyl ring, R$^3$ is methyl or phenyl, X is N—Z, Z is an amino protecting group as defined above, preferably a group of the formula SO$_2$R$^a$ wherein R$^a$ is phenyl.

In a preferred embodiment of the invention, the cyclocarbonylation reaction is carried out in the presence of a base, an anhydride and a catalyst comprising a transition metal compound and a ligand.

Transition metal compounds useful for the process of the present invention comprise salts of Pd, Pt, Ru, Co, Rh or Ni and also includes Pd/C. The use of transition metal compounds as catalysts has been described for example in Matsuzaka et al. (1988) J. Org. Chem. 53, 3832. Preferred transition metal compounds are salts of palladium, e.g. Pd(OAc)$_2$, Pd$_2$dba$_3$, PdCl$_2$, Pd$_2$Cl$_2$(π-allyl)$_2$, PdCl$_2$(NCMe)$_2$, [Pd(NCMe)$_4$](BF$_4$)$_2$, and most preferably Pd(OAc)$_2$. The mentioned catalysts are known in the art (e.g. U.S. Pat. No. 5,380,861; "Carbonylation, Direct Synthesis of Carbonyl Compounds", H. M. Colquhoun, D. J. Thompson, M. V. Trigg, Plenum Press, 1991) and/or are commercially available (e.g. from Fluka, Buchs, Switzerland or Strem Chemicals, Kehl, Germany).

The ligand of the transition metal compound in the catalyst may be selected from a group consisting of phosphine, arsine or stibine derivatives, preferably phosphine derivatives of general formulae P(R$^5$)(R$^6$)(R$^7$), (R$^5$)(R$^6$)P—(Y)—P(R$^5$)(R$^6$), As(R$^5$)(R$^6$)(R$^7$) or Sb(R$^5$)(R$^6$)(R$^7$), preferably P(R$^5$)(R$^6$)(R$^7$), wherein Y, R$^5$, R$^6$, and R$^7$ are defined below.

Especially suitable ligands are chiral and non-chiral mono- and diphosphorus compounds for example described in Houben-Weyl, "Methoden der organischen Chemie", vol. E1, page 106 et seq. Georg Thieme Verlag Stuttgart, 1982, and Aspects Homog. Catal., 4, 145–202 (1981), especially those of the formulae

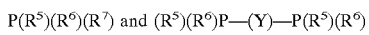

wherein $R^5$, $R^6$ and $R^7$ each independently are $C_{1-8}$-alkyl, cyclohexyl, benzyl, naphthyl, 2- or 3-pyrrolyl, 2- or 3-furyl, 2- or 3-thiophenyl, 2- or 3- or 4-pyridyl, phenyl or phenyl which is substituted by $C_{1-4}$-alkyl, $C_{1-4}$-alkoxy, halogen, trifluoromethyl, lower-alkylydenedioxy or phenyl and Y is binaphthyl, 6,6'-dimethyl- or 6,6'-dimethoxybiphenyl-2,2'-diyl, or one of the groups —$(CH_2)_n$—, —$CH_2CH_2$—P$(C_6H_5)$—$CH_2$ $CH_2$—, (IV)

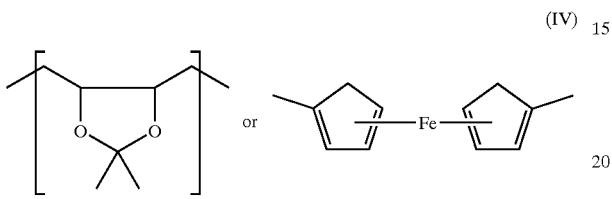

and n is a number of 1–8.

Examples of suitable phosphorus ligands are triphenylphosphine and the ligands shown in Scheme 1.

Scheme 1

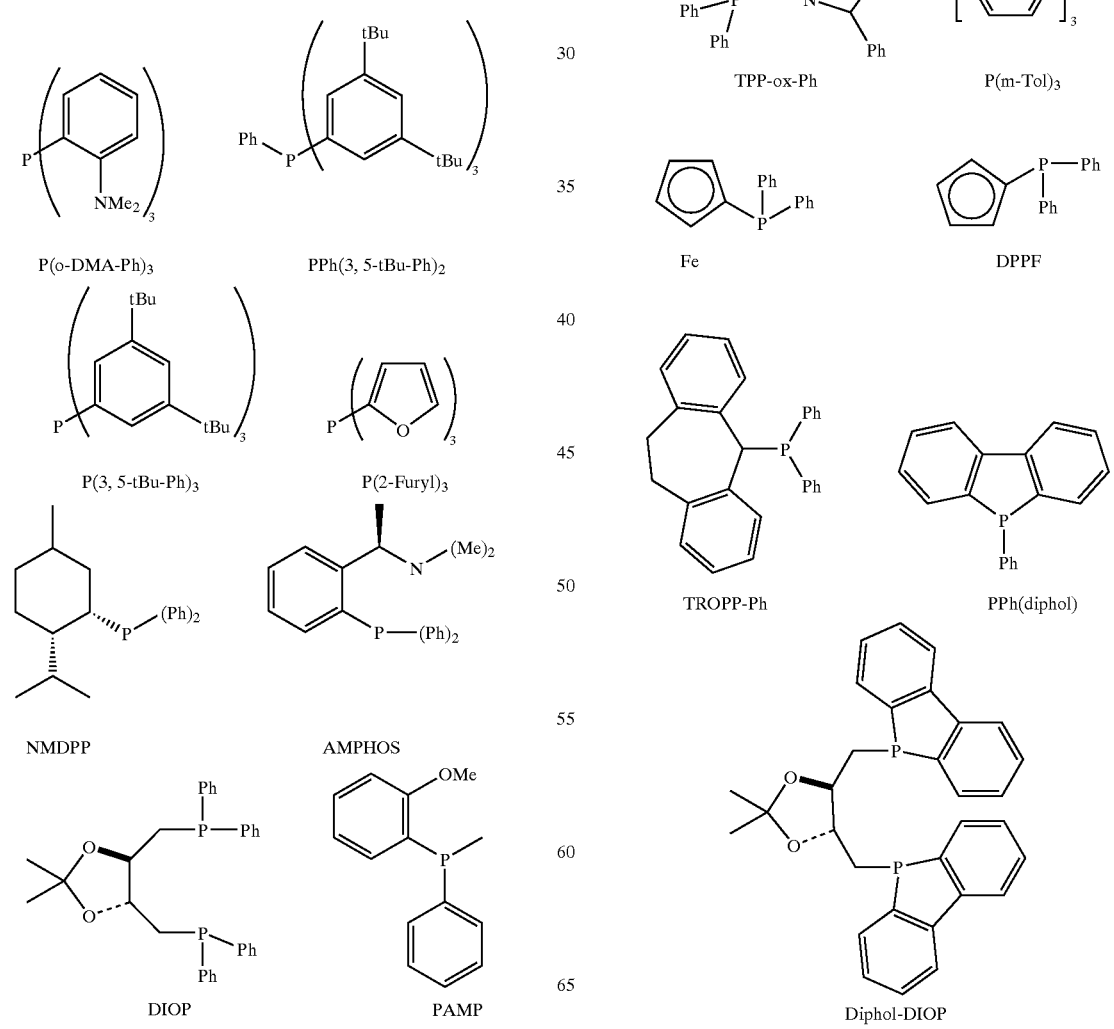

Preferred phosphorus ligands are triphenylphosphine,

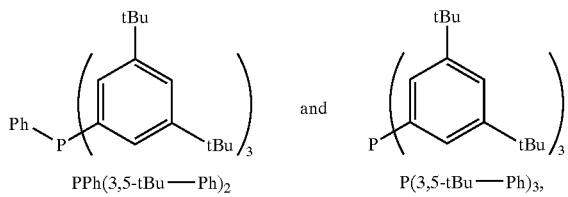

PPh(3,5-tBu—Ph)₂ and P(3,5-tBu—Ph)₃, the most preferred phosphorus ligand is triphenylphosphine.

The preparation of a transition metal complex is explained in more detail for the corresponding palladium-phosphine complex: The palladium-phosphine complex compound is conveniently formed in situ from a palladium component and a phosphine ligand. These palladium components is for example metallic palladium, which is optionally supported on a carrier material such as carbon, or a complex or a salt of 0-, 2- or 4-valent palladium such as palladium-bis(dibenzylideneacetone), palladium chloride, palladium acetate and the like. For the in situ preparation, the phosphorus ligand/transition metal compound ratio (mol/mol; P/Pd) amounts to about 0.1:1 to 100:1 preferably to about 6:1 to 15:1. Suitable phosphine ligands are for example chiral and non-chiral mono- and diphosphorus compounds such as are described in Houben-Weyl, Methoden der organischen Chemie, volume E1, page 106 et. seq. Georg Thieme Verlag Stuttgart, 1982, and Aspects Homog. Catal., 4, 145–202 (1981), especially those described above.

For the in situ preparation of the palladium-phosphine complex compound palladium-(II) chloride or palladium-(II) acetate, palladium-dichloro-bis(acetonitrile) and triarylphosphine may be used.

Further, the process of the present invention comprises the use of bases for the cyclocarbonylation reaction like tertiary bases such as tri-alkyl-amines, di-alkyl-aryl-amines, pyridines, alkyl-N-piperidines, and for example inorganic bases such as NaOH, KOH or salts of carbonic acids. Examples are (alkyl)₃amines, e.g. triethylamine, ethyl-diisopropyl-amine, pyridine, N-methyl-piperidine, sodium hydrogen carbonate, potassium hydrogen carbonate, di-sodium carbonate, etc. The preferred base is triethylamine.

The process of the present invention also comprises the use of an anhydride of the formula (R⁴(C=O))₂O for the cyclocarbonylation reaction. Examples of anhydrides in connection with the present invention are acetic anhydride, propionic anhydride, butyric anhydride, isobutyric anhydride, pivalic anhydride, benzoic anhydride etc. The preferred anhydrides are acetic anhydride and benzoic anhydride.

Solvents for the above reaction are known to skilled persons. Preferred solvents are aromatic solvents, e.g. toluene, xylene, benzene, halogenated hydrocarbons, e.g. $CH_2Cl_2$, nitrites, e.g. acetonitrile, ester, e.g. ethylacetate, amides, e.g. DMF, ether, e.g. THF, dioxane, urethanes, e.g. TMU, sulfoxides, e.g. DMSO, and mixtures thereof. The preferred solvent is toluene.

The reaction conditions for the above carbonylation reaction can vary to a certain extent.

The temperature can vary between 40° C. and 170° C., preferably between 60–120° C., and most preferably the reaction is performed at about 90° C.

The substrate/catalyst ratio (mol/mol; S/Pd) amounts to 1 to 10,000, preferably 100 to 5,000, more preferably 100 to 1,500 and most preferably 100 to 1,000.

For the in situ preparation, the above mentioned phosphorus ligand/transition metal compound ratio (mol/mol; P/Pd) amounts to 0.1:1 to 100:1, preferably 6:1 to 15:1.

The upper limit for the carbon monoxide (CO) pressure is only limited by the specification of the autoclave used. For the lower pressure limit the carbonylation reaction would work even with a CO pressure of 1 bar. Preferably, the CO pressure is about 20 to 70 bar, more preferably 35 to 60 bar.

It has been found that the "crude" compound of formula (II) can be used for the preparation of the compound of formula (I). A preparation of a crude material is performed by collecting a compound of formula (II), e.g. acetic acid 1-(1-benzenesulfonyl-1H-indol-2-yl)-allyl ester, with an organic solvent and drying without further purification. The preparation of this material is exemplified in Examples 2 and 3, Example 5 shows the use of the crude starting material for the preparation of a compound of formula (I).

The cyclocarbonylation reaction is followed by saponification. Conditions for saponification reactions are known in the art and described for example in "Practical Organic Chemistry", A. I. Vogel, Longmans Ed., 1967, p. 390–393. In a preferred embodiment of the present invention, the saponification is carried out in a biphasic mixture of aqueous sodium hydroxide and toluene or in an homogeneous mixture of sodium methylate in methanol.

Compounds of formula (II) may be prepared by methods analogous to those known in the art, for example by reaction of compounds of formula (V)

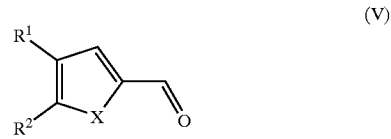

(V)

wherein $R^1$, $R^2$ and X are as defined above;

with a reagent of the formula vinyl-metal-X with -metal-X being —MgCl, —MgBr, —MgI or —Li, followed by reaction with an acid derivative selected from a group consisting of $(R^3—CO)_2O$, or $R^3—(CO)—Hal$, wherein $R^3$ is as defined above and Hal is Cl or Br.

Compounds of formula (V) are commercially available or can be prepared from compounds of formula (Va)

(Va)

by methods analogous to those known in the art.

Preferably, the compounds of formula (II) may be prepared by reaction of compounds of formula (VI)

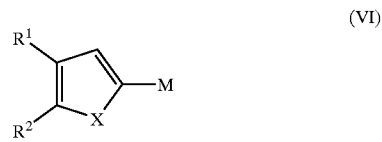

(VI)

wherein $R^1$, $R^2$ and X are as defined above and M is —MgCl, —MgBr, —MgI or —Li;

with acrolein, followed by reaction with an acid derivative selected from a group consisting of $(R^3—CO)_2O$ $R^3—(CO)—Hal$, wherein R3 is as defined above and Hal is Cl or Br.

Compounds of formula (VI) are commercially available or can be prepared from compounds of formula (VIa) or compounds of formula (VIb)

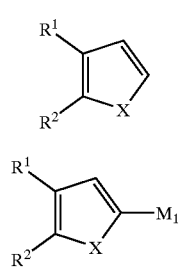

(VIa)

(VIb)

wherein $M_1$ is chloro, bromo or iodo;
by methods analogous to those known in the art.

In a preferred embodiment, the present invention relates to a process for the preparation of 4-hydroxycarbazole or N-protected 4-hydroxycarbazole. N-protected 4-hydroxycarbazole can be prepared by a cyclocarbonylation reaction as described above starting from a compound of above formula (II), wherein $R^1$ and $R^2$ together with the ring carbon atoms to which they are attached form a phenyl ring, $R^3$ is as defined above, X is N—Z and Z is an amino protecting group selected from $SO_2R^a$, $NMe_2$, $CO_2R^b$ and $CON(R^c)_2$ (with $R^a$, $R^b$ and $R^c$ being as defined above), in the presence of an anhydride and a base as defined above, followed by saponification. N-protected 4-hydroxycarbazole can be converted to 4-hydroxycarbazole by deprotection as described below. 4-Hydroxycarbazole and N-protected 4-hydroxycarbazole are useful for the preparation of pharmaceutically active substances, e.g. 1-(9H-carbazol-4-yloxy)-3-[[2-(2-methoxyphenoxy)ethyl]amino]-2-propanol (carvedilol) and optionally salts thereof. A process for the preparation of this compound has been described for example in European Patent Application EP 0 004920.

In addition, this compound may be prepared according to the following processes: In a first step, a compound of above formula (I), wherein $R^1$ and $R^2$ together with the ring carbon atoms to which they are attached form a phenyl ring, X is N—Z and Z is an amino protecting group selected from $SO_2R^a$, $NMe_2$, $CO_2R^b$ and $CON(R^c)_2$ (with $R^a$, $R^b$ and $R^c$ being as defined above), may be converted into a compound of formula (VII)

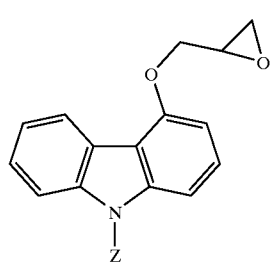

(VII)

wherein Z is as defined above, by reaction with epichlorohydrin under basic conditions. The reaction may be performed in polar organic solvents like THF, DMF or DMSO, preferably without a solvent in a great surplus of epichlorohydrin. Basic compounds are for example sodium carbonate, potassium carbonate, sodium hydride, potassium hydroxide and sodium hydroxide, preferably sodium hydroxide. The temperature can vary between 20° C. and 100° C., with a preferred temperature between 40–60° C.

The above process may be followed by conversion of the compound of formula (VII) into a compound of formula (VIII)

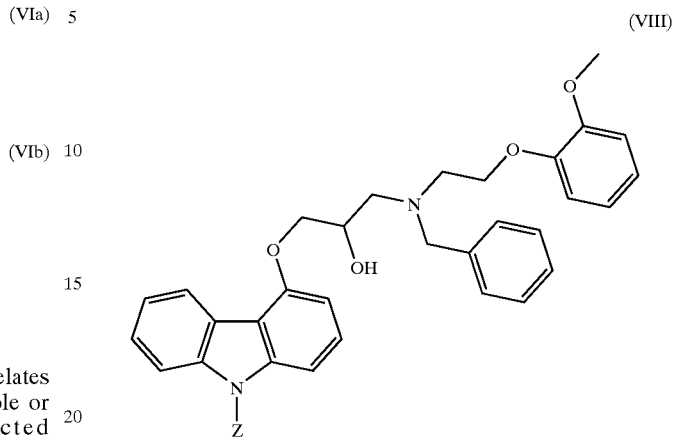

(VIII)

wherein Z is as defined above, by reaction with benzyl-[2-(2-methoxy-phenoxy]-ethyl-amine. The reaction may be performed in organic solvents like ethanol, methanol, isopropanol, THF and DMF, preferably with ethanol. The temperature can vary between 40 and 140° C., with a preferred temperature between 60–90° C.

Deprotection of the compound of formula (VIII) reveals 1-{benzyl-[2-(2-methoxyphenoxy)-ethyl]-amino}-3-(9H-carbazol-4-yloxy)-propan-2-ol of formula (IX)

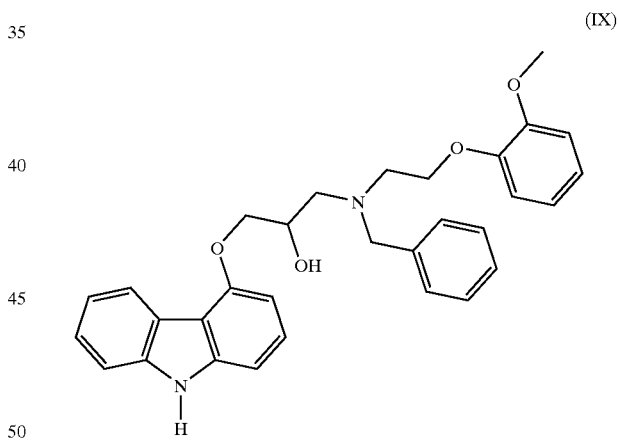

(IX)

Methods of deprotection reactions are known in the art and described for example in P. J. Kocienski, Protecting Groups, Thieme 1994. From a compound of above formula (VIII) for example, wherein Z is $SO_2R^a$ and $R^a$ is phenyl, 1-{benzyl-[2-(2-methoxy-phenoxy)-ethyl]-amino}-3-(9H-carbazol-4-yloxy)-propan-2-ol of formula (IX) can be synthesized under basic conditions in organic solvents like ethanol, methanol, isopropanol, THF and DMF or mixtures of these solvents, preferably with a mixture of THF and methanol. Basic compounds are for example potassium hydroxide, sodium hydroxide and potassium tert-butoxide, preferably sodium hydroxide. The temperature can vary between 20° C. and 100° C., with a preferred temperature between 40–60° C.

Hydrogenation of the compound of formula IX reveals 1-(9H-carbazol-4-yloxy)-3-[[2-(2-methoxyphenoxy)ethyl]amino]-2-propanol (carvedilol) of formula (X). The reaction may be performed in organic solvents like ethanol, methanol, isopropanol and THF, preferably with methanol. The pressure of hydrogen can vary between 1 bar and 50 bar pressure, with a preferred hydrogen pressure between 1 to 10 bar. The temperature can vary between 20° C. and 100° C., with a preferred temperature between 40–60° C.

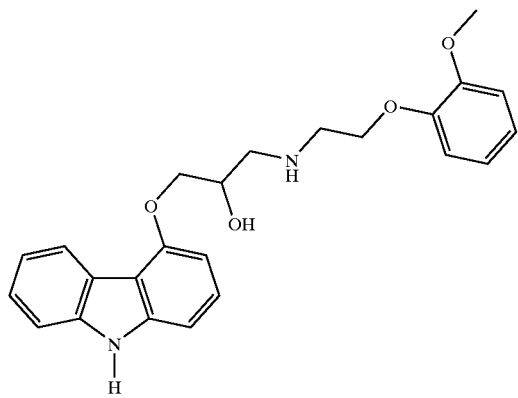

(X)

Another embodiment of the present invention relates to a process for the preparation of 1-(9H-carbazol-4-yloxy)-3-[[2-(2-methoxyphenoxy)ethyl]amino]-2-propanol comprising:

cyclocarbonylation of acetic acid 1-(1-benzenesulfonyl-1H-indol-2-yl)allyl ester or benzoic acid 1-(1-benzenesulfonyl-1H-indol-2-yl)-allyl ester to give acetic acid 9-benzenesulfonyl-9H-carbazol-4-yl ester;

saponification of acetic acid 9-benzenesulfonyl-9H-carbazol-4-yl ester to give 9-benzenesulfonyl-9H-carbazol-4-ol;

reaction of 9-benzenesulfonyl-9H-carbazol-4-ol with epichlorohydrin under basic conditions to give 9-benzenesulfonyl-4-oxiranylmethoxy-9H-carbazole;

reaction of 9-benzenesulfonyl-4-oxiranylmethoxy-9H-carbazole with benzyl-[2-(2-methoxy-phenoxy]-ethyl-amine to give a 1-(9-benzenesulfonyl-9H-carbazol-4-yloxy)-3-{benzyl-[2-(2-methoxy-phenoxy)ethyl]-amino}-propan-2-ol;

deprotection of 1-(9-benzenesulfonyl-9H-carbazol-4-yloxy)-3-{benzyl-[2-(2-methoxy-phenoxy)ethyl]-amino}-propan-2-ol under basic conditions to give 1-{benzyl-[2-(2-methoxy-phenoxy)-ethyl]-amino}-3-(9H-carbazol-4-yloxy)-propan-2-ol;

hydrogenation of 1-{benzyl-[2-(2-methoxy-phenoxy)-ethyl]-amino}-3-(9H-carbazol-4-yloxy)-propan-2-ol in an organic solvent to give 1-(9H-carbazol-4-yloxy)-3-[[2-(2-methoxyphenoxy)ethyl]amino]-2-propanol of formula (X).

The above process for the preparation of 1-(9H-carbazol-4-yloxy)-3-[[2-(2-methoxyphenoxy)ethyl]amino]-2-propanol (carvedilol) may alternatively be performed in an analogous manner starting from 4-hydroxycarbazole of formula (XI)

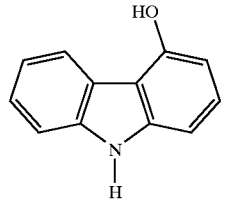

(XI)

instead of N-protected 4-hydroxycarbazole.

A compound of above formula (I), wherein $R^1$ and $R^2$ together with the ring carbon atoms to which they are attached form a phenyl ring, X is N—Z and Z is an amino protecting group selected from $SO_2R^a$, $NMe_2$, $CO_2R^b$ and $CON(R^c)_2$ (with $R^a$, $R^b$ and $R^c$ being as defined above), may be converted into 4-hydroxycarbazole formula (XI) by deprotection. Methods of deprotection reactions are known in the art and described for example in P. J. Kocienski, Protecting Groups, Thieme 1994. From a compound of above formula (I) for example, wherein $R^1$ and $R^2$ together with the ring carbon atoms to which they are attached form a phenyl ring, X is N—Z, Z is $SO_2R^a$ and $R^a$ is phenyl, 4-hydroxy-carbazole can be synthesized under basic conditions in organic solvents like ethanol, methanol, isopropanol, THF and DMF or mixtures of these solvents, preferably with THF. Basic compounds are for example potassium hydroxide, sodium hydroxide, sodium methoxide, sodium tert.-butoxide and potassium tert.-butoxide, preferably potassium tert.-butoxide. The temperature can vary between 10° C. and 100° C., with a preferred temperature between 20° C. and 40° C.

4-hydroxy-carbazole (XI) may be converted into a compound of formula (XII) by reaction with epichlorohydrin under basic conditions. The reaction may be performed in polar organic solvents like THF, DMF or DMSO, preferably without a solvent in a great surplus of epichlorohydrin. Basic compounds are for example sodium carbonate, potassium carbonate, sodium hydride, potassium hydroxide and sodium hydroxide, preferably sodium hydroxide. The temperature can vary between 20° C. and 100° C., with a preferred temperature between 40–60° C.

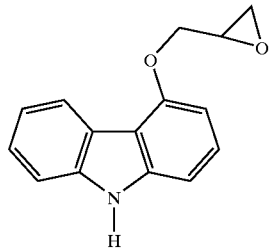

(XII)

The above process may be followed by conversion of the compound of formula (XII) into a compound of formula (IX)

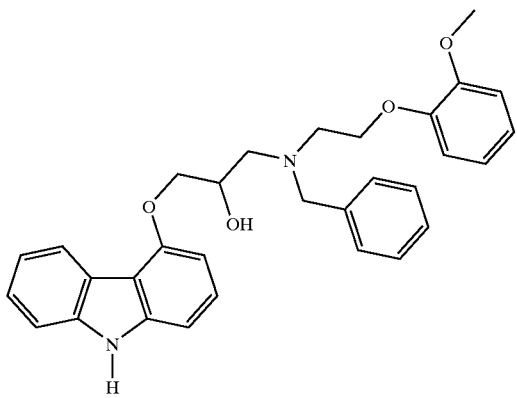

(IX)

by reaction with benzyl-[2-(2-methoxy-phenoxy]-ethyl-amine. The reaction may be performed in organic solvents like ethanol, methanol, isopropanol, THF and DMF, preferably with ethanol. The temperature can vary between 40 and 140° C., with a preferred temperature between 60–90° C.

Hydrogenation of the compound of formula IX reveals 1-(9H-carbazol-4-yloxy)-3-[[2-(2-methoxyphenoxy)ethyl]amino]-2-propanol(carvedilol) of formula (X)

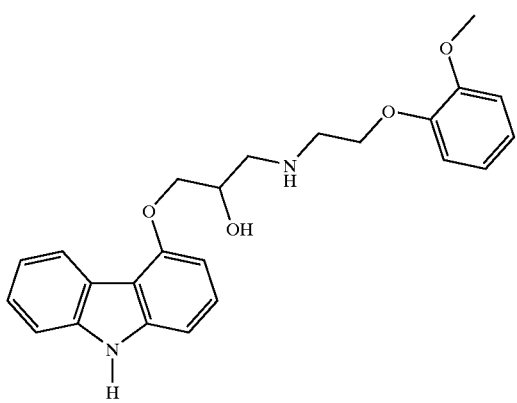

(X)

This reaction may be performed as described above.

Another embodiment of the present invention relates to a process for the preparation of 1-(9H-carbazol-4-yloxy)-3-[[2-(2-methoxyphenoxy)ethyl]amino]-2-propanol comprising:
cyclocarbonylation of acetic acid 1-(1-benzenesulfonyl-1H-indol-2-yl)allyl ester or benzoic acid 1-(1-benzenesulfonyl-1H-indol-2-yl)-allyl ester to give acetic acid 9-benzenesulfonyl-9H-carbazol-4-yl ester;
saponification of acetic acid 9-benzenesulfonyl-9H-carbazol-4-yl ester to give 9-benzenesulfonyl-9H-carbazol-4-ol;
deprotection of 9-benzenesulfonyl-9H-carbazol-4-ol to give 4-hydroxy-carbazole reaction of 4-hydroxy-carbazole with epichlorohydrin under basic conditions to give 4-oxiranylmethoxy-9H-carbazole;
reaction of 4-oxiranylmethoxy-9H-carbazole with benzyl-[2-(2-methoxy-phenoxy]-ethylamine to give a 1-{benzyl-[2-(2-methoxy-phenoxy)-ethyl]-amino}-3-(9H-carbazol-4-yloxy)propan-2-ol;
hydrogenation of 1-{benzyl-[2-(2-methoxy-phenoxy)-ethyl]-amino}-3-(9H-carbazol-4-yloxy)-propan-2-ol in an organic solvent to give 1-(9H-carbazol-4-yloxy)-3-[[2-(2-methoxyphenoxy)ethyl]amino]-2-propanol of formula (X).

In a further embodiment, the present invention relates to the use of any of the above processes for the preparation of 1-(9H-carbazol-4-yloxy)-3-[[2-(2-methoxyphenoxy)-ethyl]-amino]-2-propanol and optionally salts thereof.

The compounds of formula (IIa)

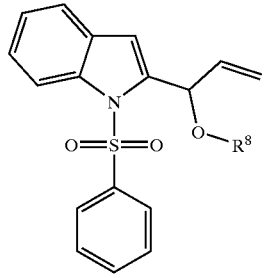

(IIa)

wherein $R^8$ is hydrogen, acetyl or benzoyl, are preferred educts of the processes according to the present invention. These compounds are new and are also subject of the present invention.

The following examples shall illustrate preferred embodiments of the present invention but are not intended to limit the scope of the invention.

EXAMPLES

Example 1

1-(1-Benzenesulfonyl-1H-indol-2-yl)-allyl alcohol 10.3 g (40 mmol) of 1-(phenylsulfonyl)indole (synthesized analogous to T. Sakamoto; Y. Kondo; N. Takazawa; H. Yamanaka; J.Chem.Soc.Perkin Trans.1; 16; 1996; 1927–1934) in 110 ml tetrahydrofuran were cooled to −20° C. To the stirred solution 30 ml of 1.6 M n-butyllithium were added at −20° C. within 20 min. The resulting suspension was warmed to 10° C. and stirred at 10° C. for 4 hours. The mixture was again cooled to −20° C. and a solution of 3.4 g acrolein (61 mmol) in 20 ml THF was added dropwise within 20 min at −20° C. The solution was stirred at 20° C. for 16 hours. 150 ml water was added dropwise, the mixture was vigorously stirred for 10 min. The phases were separated, and the water phase was extracted with 3×100 ml of methyl-t-butyl-ether. The combined organic phases were washed with 100 ml of brine, dried on sodium sulfate and rotary evaporated (35° C., 20 mbar). The residue was purified by liquid chromatography (eluent toluene/ethyl acetate 6:1), the pure fractions were collected and rotary evaporated (40° C./15 mbar).

Yield: 10.0 g (80%).

1H NMR (δ, DDMSO): 5.78 (OH, d), 5.86 (C$\underline{H}$—O, dd), 6.20 (C$\underline{H}$=CH2, ddd), 5.19 (CH=C$\underline{H}$2, dd), 5.40 (CH=C$\underline{H}$2, dd), aromatic signals at 6.7–8.1.

Example 2

Acetic acid 1-(1-benzenesulfonyl-1H-indol-2-yl)-allyl ester

To a solution of 19.1 g of 1-(1-benzenesulfonyl-1H-indol-2-yl)-allyl alcohol (74 mmol) in 244 ml dichloromethane were added 34 ml triethylamine and 0.7 g 4-dimethyl-aminopyridine. The solution was cooled to 3° C. To the magnetically stirred solution 23.5 ml of acetic anhydride qas added with a dropping funnel at a temperature below 5° C.

The reaction mixture was stirred 2 h at 22° C. After cooling in an ice bath 250 ml of water was added at a temperature of 20 to 24° C. The mixture was vigorously stirred for 10 min. The phases were separated, and the water solution extracted with 250 ml of dichloromethane. The combined organic phases were extracted with 250 ml of water three times, and once with 250 ml of brine. The dichloromethane solution was dried on sodium sulfat and finally rotary evaporated (35° C., 50 mbar), yield 22.8 g. In the next step (the cyclocarbonylation) the resulting oil was used without purification (crude quality).

1H NMR (δ, DDMSO): 2.07 (C$\underline{H}$3-CO, s), 6.87 (C$\underline{H}$—O, d), 6.19 (C$\underline{H}$=CH2, ddd), 5.37 (CH=C$\underline{H}$2, dd), 5.38 (CH=C$\underline{H}$2, dd), aromatic signals at 6.9–8.0.

Example 3
Benzoic acid 1-(1-benzenesulfonyl-1H-indol-2-yl)-allyl ester

To a stirred solution of 10.0 g of 1-(1-benzenesulfonyl-1H-indol-2-yl)-allyl alcohol (32 mmol) in 100 ml of pyridine were added dropwise 5,6 ml benzoyl chloride (48 mmol) at 10° C. The mixture was stirred for an additional 1 h at 20° C. Most of the pyridine was distilled off, the residue was given in portions to 300 ml of ice water. The pH was adjusted to 2–3 with conc. HCl. The water was distilled off and the residue was dissolved in 100 ml of diethyl ether. After about 1 h the product crystallized. The suspension was stirred in an ice bath for 2 h, the solid was filtered off. The crude material was recrystallized from 90 ml methanol and dried 12 h at 35° C.

Yield: 5.2 g (39%) HPLC 98,4 Area-%, m.p. 112–114° C.

1H NMR (δ, DDMSO): 7.19 (C$\underline{H}$—O, d), 6.35 (CH=C$\underline{H}$2, ddd), 5.44 (CH=C$\underline{H}$2, dd), 5.48 (CH=C$\underline{H}$2, dd), aromatic signals at 7.0–8.1.

Example 4
Acetic acid 1-(1-benzenesulfonyl-1H-indol-2-yl)-allyl ester

To a solution of 2.9 g (10 mmol) of 1-benzenesulfonyl-1H-indole-2-carbaldehyde (synthesized analogous to M. G. Saulnier, G. W. Gordon, J. Org. Chem.; 47; 5; 1982, 757–761) in 10 ml of tetrahydrofuran was added 6.5 ml of vinylmagnesium chloride 1.7 M solution in THF at −20° C. within 1 h. The temperature increased to 0° C. within 30 min and kept at this temperature for 20 min. To the suspension 1.3 ml acetic anhydride (14 mmol was added at 0° C. within 15 min. The cooling bath was removed and after stirring for 1 h at 20° C. 10 ml water was added at 10–15° C. The mixture was stirred for an additional 1 h at 20° C. The phases were separated, and the aqueous phase was extracted with 20 ml of ethyl acetate. The combined organic phases were washed with 20 ml of brine, dried on sodium sulfate and rotary evaporated (35° C., 12 mbar). The crude material was purified by liquid chromatography (eluent isohexane/ethyl acetate 9:1).

Yield: 3.9 g, with a 60% purity according to NMR analysis.

1H NMR (δ, DDMSO): 2.07 (C$\underline{H}$3-CO, s), 6.87 (C$\underline{H}$—O, d), 6.19 (C$\underline{H}$=CH2, ddd), 5.37 (CH=C$\underline{H}$2, dd), 5.38 (CH=C$\underline{H}$2, dd), aromatic signals at 6.9–8.0.

Example 5
Cyclocarbonylation of acetic acid 1-(1-benzenesulfonyl-1H-indol-2-yl)-allyl ester (Crude Quality)

An autoclave was charged under an argon flow with 1.066 g of acetic acid 1-(1-benzenesulfonyl-1H-indol-2-yl)-allyl ester (3.0 mmol, oil, crude quality), 0.57 ml of acetic anhydride (6.0 mmol), 0.92 ml of triethylamine (6.6 mmol) and 2.5 ml of a catalyst solution prepared from 6.73 mg of palladium acetate (0.030 mmol) and 78.7 mg of triphenylphosphine (0.30 mmol) in 25 ml of toluene. Then the autoclave was sealed, pressurized three times with 20 bar of carbon monoxide and vented, and finally pressurized with 50 bar of carbon monoxide. The reaction mixture was stirred magnetically and heated at 90° C. for 20 h. After cooling and venting the autocave, the dark reaction mixture was poured onto ice water and the biphasic solution stirred vigorously for 1 h. The aqueous phase was extracted with 20 ml of toluene, whereas the toluene phase was extracted in a separatory funnel with 10 ml of water and 10 ml of brine. The combined toluene phases were dried on sodium sulfate and finally rotary evaporated (47° C., 10 mbar). The resulting brown residue was purified by chromatography on silica gel (eluent: cyclohexane/tbutyl methyl ether 2:1 vol/vol) to afford 960 mg (88%) of acetic acid 9-benzenesulfonyl-9H-carbazol-4-yl ester as a light brown oil.

1H NMR (δ, CDCl$_3$): 2.48 (OAc, singlet), aromatic signals at 7.2–8.4.

Example 6
Saponification of Acetic Acid 9-benzenesulfonyl-9H-carbazol-4-yl ester A solution of 0.96 g of acetic acid 9-benzenesulfonyl-9H-carbazol-4-yl ester (2.62 mmol) in 15 ml of methanol was treated with 3.5 ml of 4 M sodium hydroxide (14 mmol) and stirred at 50° C. for 1.5 h. After cooling to room temperature, methanol was removed from the reaction mixture by rotary evaporation and the residue was partitioned between t-butyl methyl ether and 2N aq. HCl. After drying (Na$_2$SO$_4$) the organic phase was evaporated to dryness to afford 0.84 g (99%) of 9-benzenesulfonyl-9H-carbazol-4-ol as an orange brown oil.

1H NMR (δ, CDCl$_3$): 5.6 (OH, broad), 6.7 (1H, d), other aromatic signals at 7.3–8.4.

Example 7
Removal of Sulfonyl Protecting Group

A solution of 0.83 g of 9-benzenesulfonyl-9H-carbazol-4-ol (2.57 mmol) in 18 ml of tetrahydrofuran was treated with 2.88 g of potassium tert.butoxide (25.7 mmol) and the suspension stirred at room temperature under argon over night. Then 2N hydrochloric acid solution was added until the pH was 3 and the resulting brown solution was partitioned between 20 ml of tert.butyl methyl ether and 5 ml of water. After drying on sodium sulfate, the organic phase was rotary evaporated (50° C./10 mbar) to give 500 mg of a dark oil, which according to HPLC analysis (Symmetry C8 column 5 μm 250×4.6 mm, eluted with a mixture of phosphate buffer at pH 7/acetonitrile/water 2:1:7 (40%) and acetonitrile (60%); retention time 4.2 min) had 70% content of 4-hydroxy-9H-carbazole.

1H NMR (δ, CDCl$_3$): 5–5.5 (OH, very broad), 6.5 (1H, d), 8.0 (NH, broad), other aromatic signals at 6.9–8.2.

Treatment of the oil with charcoal (Darco KB-B) in methanol for 1 h at room temperature, filtration and evaporation afforded 4-hydroxy-9H-carbazole as a light brown solid, which could be purified by crystallization from toluene.

Example 8
Synthesis of 9-benzenesulfonyl-9H-carbazol-4-ol Starting from Crystallized acetic acid 1-(1-benzenesulfonyl-1H-indol-2-yl)-allyl ester 16.60 g of acetic acid 1-(1-benzenesulfonyl-1H-indol-2-yl)-allyl ester (46.7 mmol, crude quality) were crystallized from 20 ml of diisopropyl ether and 10 ml of hexane at 2° C. Filtration afforded 12.7 g (76%) of pure acetic acid 1-(1-benzenesulfonyl-1H-indol-2-yl)-allyl ester as slightly beige crystals with a m.p. of 81–84° C. 9.953 g of this material were subjected to the cyclocarbonylation reaction in analogy to example 1, affording after work-up 10.62 g of acetic acid 9-benzenesulfonyl-9H-carbazol-4-yl ester as a light brown oil with a purity 91% according to HPLC analysis (94.4% isolated yield). 10.50 g of this material was subjected to saponification without further purification in analogy to example 6, affording 9.60 g of 9-benzenesulfonyl-9H-carbazol-4-ol as an orange-brown crystalline material with a 85% purity according to HPLC. Thus, the overall yield over both steps was 90.8%.

Example 9

Cyclocarbonylation of benzoic acid 1-(1-benzenesulfonyl-1H-indol-2-yl)-allyl ester An autoclave was charged under an argon flow with 4.17 g of benzoic acid 1-(1-benzenesulfonyl-1H-indol-2-yl)-allyl ester (10.0 mmol), 1.89 ml of acetic anhydride (20.0 mmol), 3.08 ml of triethylamine (22.0 mmol), 15 ml of toluene and 5.0 ml of a catalyst solution prepared from 9.0 mg of palladium acetate (0.04 mmol) and 105 mg of triphenylphosphine (0.40 mmol) in 20 ml of toluene. Then the autoclave was sealed, pressurized three times with 20 bar of carbon monoxide and vented, and finally pressurized with 50 bar of carbon monoxide. The reaction mixture was stirred magnetically and heated at 90° C. for 20 h. After cooling and venting the autocave, the dark reaction mixture was poured onto ice water and the biphasic solution stirred vigorously for 1 h. The toluene phase was extracted twice with sodium bicarbonate half-saturated solution, then the combined organic phases were extracted with 20 ml of toluene, dried on sodium sulfate and finally rotary evaporated (47° C., 10 mbar). The resulting orange oily residue (4.15 g, 91% yield) was acetic acid 9-benzenesulfonyl-9H-carbazol-4-yl ester with a 80% purity according to HPLC analysis. MS: 365.0 ($M^+$).

Example 10

Saponification of acetic acid 9-benzenesulfonyl-9H-carbazol-4-yl ester

Treatment of 4.15 g of acetic acid 9-benzenesulfonyl-9H-carbazol-4-yl ester (prepared in example 9) in an analogous manner as described in example 6 afforded 4.15 g of 9-benzenesulfonyl-9H-carbazol-4-ol as an orange-brown crystalline material with 73% purity according to HPLC analysis.

Example 11

9-Benzenesulfonyl-4-oxiranylmethoxy-9H-carbazole

A 1l 3-necked glass flask equipped with a magnetic stirrer, a thermometer and a nitrogen inlet was charged with 23.6 g of 9-benzenesulfonyl-9H-carbazol-4-ol (73 mmol) and 236 ml of epichlorohydrin (3.0 mol) and to the resulting solution 236 ml of a 5 N sodium hydroxide solution was added in one portion at 20° C. The temperature of the oil bath was increased to 45° C., the temperature inside increased slowly to 55° C., and after 30 min the temperature inside was at 45° C. The stirring was continued for 3 h. Most of epichlorohydrin and water was distilled off with a rotary evaporator ($T_{bath}$ 50° C., 10 mbar), the residue was dissolved in a mixture of 236 ml THF and 236 ml 5 N sodium hydroxide solution and stirred for 18 h at 30° C. It was cooled to 20° C. and the phases were separated. The water phase was extracted with 300 ml of ethyl acetate, and the combined organic phases were washed with 2×300 ml of brine, dried ($Na_2SO_4$), and rotary evaporated ($T_{bath}$ 40° C., 20 mbar). The resulting brown oil was stirred in 700 ml diethyl ether for 1 h at 20° C., the product crystallized. The suspension was stirred 1 h in an ice bath, the product was filtered under suction, and washed with 50 ml cold diethyl ether. The substance was dried at 50° C. for 6 h.

Yield: 18,7 g (67.5%) of 9-benzenesulfonyl-4-oxiranylmethoxy-9H-carbazole as light brown solid, m.p. 107/108–110° C.

1H NMR (δ, DDMSO): 4.09 (C$\underline{H}$2O, dd), 4.56 (C$\underline{H}$2O, dd), 3.49 (C$\underline{H}$—O, cycle, dddd), 2.80 (C$\underline{H}$2O, cycle, dd), 2.90 (C$\underline{H}$2O, cycle, dd), aromatic signals at 6.9–8.3.

From the mother liquor additional 5.3 g substance was isolated, m.p. 100/103–107° C.

Example 12

1-(9-Benzenesulfonyl-9H-carbazol-4-yloxy)-3-{benzyl-[2-(2-methoxy-phenoxy)-ethyl]-amino}-propan-2-ol 7.4 g of benzyl-[2-(2-methoxy-phenoxy)-ethyl]-amine (29 mmol) were dissolved in 47 ml ethanol. To the stirred solution 10 g of 9-benzenesulfonyl-4-oxiranylmethoxy-9H-carbazole (26 mmol) were added and the mixture was heated under reflux for 15 h. The boiling solution was treated with 1 g of activated carbon for 30 min. The activated carbon was filtered off in the heat, and washed with 20 ml ethanol. The ethanol was rotary evaporated ($T_{bath}$ 40° C., 20 mbar) and the crude material purified by liquid chromatography (eluent toluene/ethyl acetate 4:1), the pure fractions were collected and rotary evaporated (40° C./15 mbar).

Yield: 11.1 g (67%).

1H NMR (δ, DDMSO): 4.21 (—O—C$\underline{H}$2-CH—O, dd), 4.09 (—O—C$\underline{H}$2-CH—O, m), 4.10 (—O—C$\underline{H}$2-C$\underline{H}$—O, m), 4.91 (—O$\underline{H}$, d), 2.72 (—O—CH—C$\underline{H}$2-N, dd), 2.86 (—O—CH—C$\underline{H}$2-N, dd), 3.72 (N—C$\underline{H}$2-Ph, d), 3.81 (N—C$\underline{H}$2-Ph, d), 2.89 (N—C$\underline{H}$2-CH2—O, m), 3.99 (N—CH2-C$\underline{H}$2-O, t), 3.64 (—O—C$\underline{H}$3, s), aromatic signals at 6.7–8.3.

Example 13

1-{Benzyl-[2-(2-methoxy-phenoxy)-ethyl]-amino}-3-(9H-carbazol-4-yloxy)-propan-2-ol 3.3 g of 1-(9-Benzenesulfonyl-9H-carbazol-4-yloxy)-3-{benzyl-[2-(2-methoxyphenoxy)-ethyl]-amino}-propan-2-ol (5.2 mmol) were dissolved in 33 ml THF/methanol (2:1). A solution of 1.1 g of sodium hydroxide in 1.7 ml of water was added in one portion. The mixture was stirred for 18 h at 50° C. The mixture was rotary evaporated (35° C./20 mbar). The residue was dissolved in 25 ml of toluene and 20 ml of water. The phases were separated and the toluene phase was washed 3 times with 25 ml of water. The organic phase was rotary evaporated (40° C./15 mbar) and the residue was crystallized with 9 ml ethanol. The product was filtered under suction and washed twice with 3 ml cold ethanol. The substance was dried at 50° C. for 12 h.

Yield: 1.7 g (65), m.p. 92–96° C.

Example 14

4-Oxiranylmethoxy-9H-carbazole 10.4 g of 4-hydroxy-carbazole (57 mmol) were dissolved in 31.1 ml of DMSO. 6.9 ml of epichlorohydrin (88 mmol) were added and next 57 ml of a 1 N sodium hydroxide solution. The mixture was stirred for 8 h at 40° C. It was cooled to 20° C. adn 130 ml of water were added. The product was filtered under suction, and washed with 3×30 ml water. The crude material was recrystallized from isopropanol. The substance was dried at 60° C. for 12 h.

Yield: 9.8 g (72%), m.p. 128–132° C.

Example 15

1-{Benzyl-[2-(2-methoxy-phenoxy)-ethyl]-amino}-3-(9H-carbazol-4-yloxy)-propan-2-ol 35.0 g of benzyl-[2-(2-methoxy-phenoxy)-ethyl]-amine (136 mmol) were dissolved in 225 ml ethanol. To the stirred solution 30.1 g of 4-oxiranylmethoxy-9H-carbazole (126 mmol) were added and the mixture was heated under reflux for 15 h. The boiling solution was treated with 3 g of activated carbon for 30 min. The activated carbon was filtered off in the heat, and washed with 20 ml ethanol. The solution was stirred for 3 h at room temperature and next 5 h at 0° C. The product was filtered under suction and washed twice with 10 ml cold ethanol. The substance was dried at 50° C. for 12 h Yield: 51.0 g (82%), purity 99.3% according to HPLC analysis.

Example 16

1-(9H-carbazol-4-yloxy)-3-[2-(2-methoxy-phenoxy)-ethylamino]-propan-2-ol (carvedilol)

10 g of 1-{Benzyl-[2-(2-methoxy-phenoxy)-ethyl]-amino}-3-(9H-carbazol-4-yloxy)-propan-2-ol (20 mmol) were dissolved in 80 ml methanol. 1 g of Pd—C (10%) were added and the suspension was warmed to 50° C. The mixture was hydrogenated at normal pressure for about 7 hours. The Pd-catalyst was filtered under suction and washed with 25 ml of hot methanol. 80 ml of methanol were distilled off and the residue was cooled to 0° C. and hold at this temperature for 6 h. The product was filtered and washed twice with 3 ml cold methanol. The substance was dried at 60° C. for 12 h.

Yield: 7.5 g (91%), m.p. 112–114° C.

Upon reading the present specification, various alternative embodiments will become obvious to the skilled artisan. These variations are to be considered within the scope and spirit of the subject invention, which is only to be limited by the claims that follow and their equivalents.

What is claimed is:

1. A process preparing a compound of the formula:

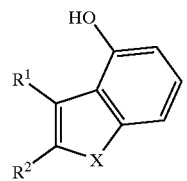

(I)

wherein $R^1$ and $R^2$ are independently selected from the group consisting of hydrogen and lower-alkyl; or $R^1$ and $R^2$ together with the ring carbon atoms to which they are attached form a monovalent carbocyclic or a monovalent carbocyclic aromatic ring or a monovalent carbocyclic or monovalent carbocyclic aromatic ring may substituted by halogen, lower-alkyl or lower-alkoxy;

X is N—Z;

Z is an amino protecting group selected from the group consisting of $SO_2R^a$, $NMe_2$, $CO_2R^b$ and $CON(R^c)_2$;

$R^a$ is lower-alkyl or aryl; and $R^b$ and $R^c$ are lower-alkyl;

which comprises:

(a) cyclocarbonylating a compound of formula:

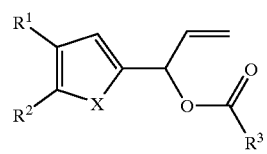

(II)

wherein $R^3$ is lower-alkyl, aryl or aralkyl, and $R^1$, $R^2$ and X are as defined above; to form a compound of formula:

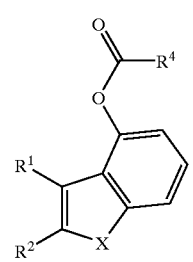

(III)

wherein $R^4$ is lower-alkyl or aryl and $R^1$, $R^2$ and X are as defined above; and (b) saponifying the compound of formula (III) to produce the compound of formula (I).

2. The process according to claim 1, wherein Z is $SO_2R^a$ and $R^a$ is phenyl.

3. The process according to claim 1, wherein $R^1$ and $R^2$ together with the ring carbon atoms to which they are attached form a phenyl ring.

4. The process according to claim 1, wherein $R^3$ is methyl or phenyl.

5. The process according to claim 1, wherein the cyclocarbonylating is carried out in the presence of a base, an anhydride, and a catalyst comprising a transition metal compound and a ligand.

6. The process according to claim 5, wherein the transition metal compound is a palladium salt.

7. The process according to claim 6, wherein the transition metal compound is selected from the group consisting of $Pd(OAc)_2$, $Pd_2dba_3$, $PdCl_2$, $Pd_2Cl_2(\square\text{-allyl})_2$, $PdCl_2(NCMe)_2$, $[Pd(NCMe)_4](BF_4)_2$ or Pd/C.

8. The process according to claim 8, wherein the transition metal compound is $Pd(OAc)_2$.

9. The process according to claim 5, wherein the ligand is $P(R^5)(R^6)(R^7)$ or $(R^5)(R^6)P—(Y)—P(R^5)(R^6)$ wherein $R^5$, $R^6$ and $R^7$ each independently are $C_{1-8}$-alkyl, cyclohexyl, benzyl, naphthyl, 2- or 3-pyrrolyl, 2- or 3-furyl, 2- or 3-thiophenyl, 2- or 3- or 4-pyridyl, phenyl or phenyl which is substituted by $C_{1-4}$-alkyl, $C_{1-4}$-alkoxy, halogen, trifluoromethyl, lower alkylydenedioxy or phenyl and Y is binaphthyl, 6,6'-dimethyl- or 6,6'-dimethoxybiphenyl-2,2'-diyl, or one of the groups —$(CH_2)_n$—, —$CH_2CH_2$—P$(C_6H_5)$—$CH_2CH_2$—,

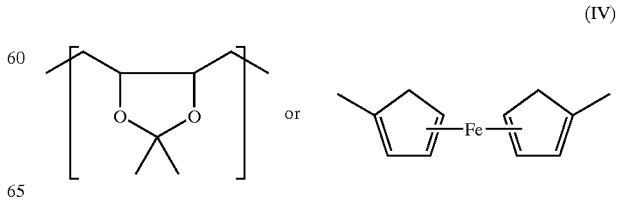

(IV)

and n is a number of 1–8.

10. The process according to claim 9, wherein the ligand is selected from the group consisting of triphenylphosphine, and

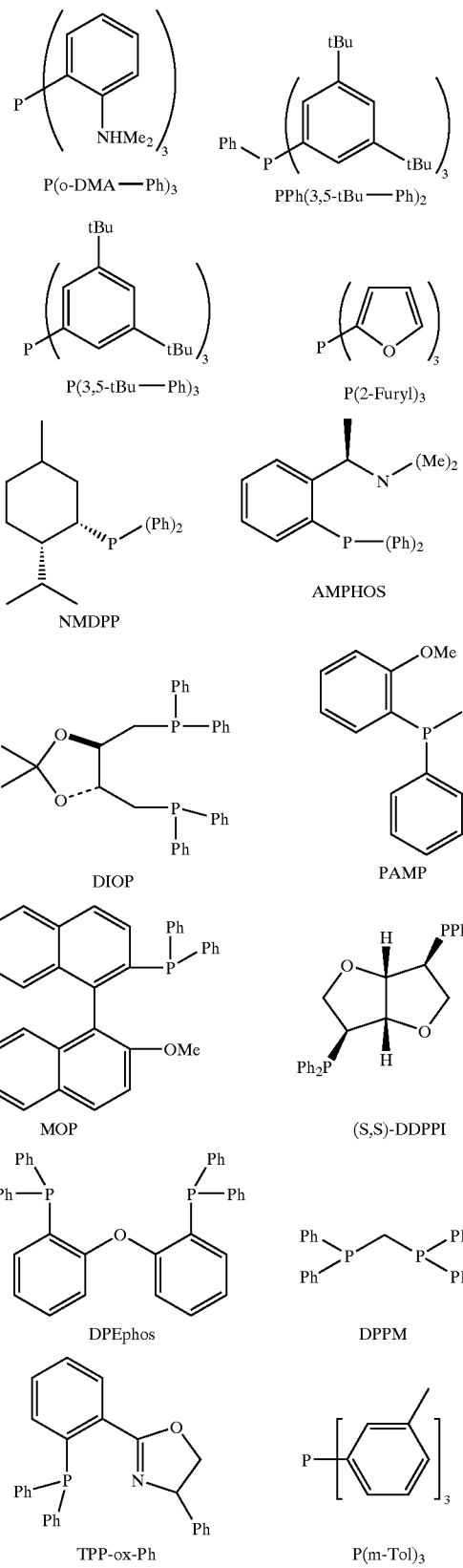

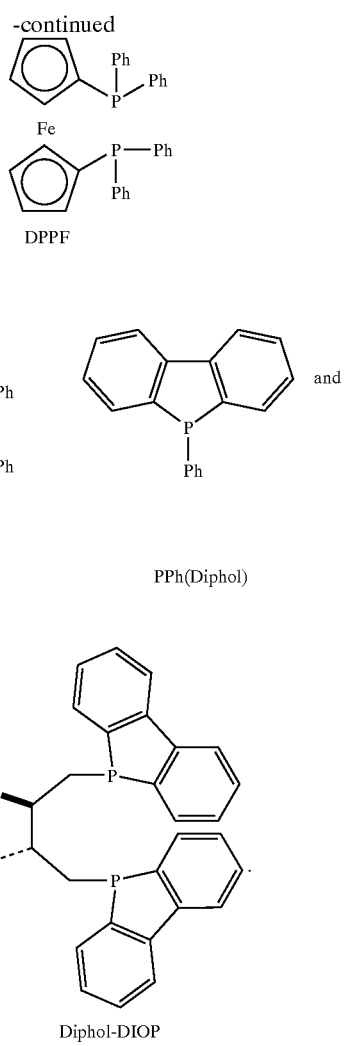

11. The process according to claim 10, wherein the ligand is triphenylphosphine,

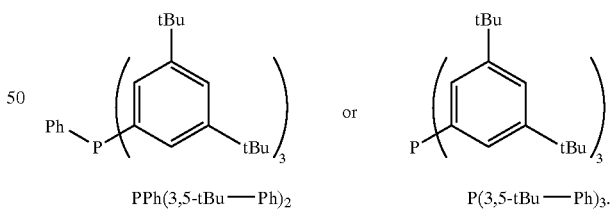

12. The process according to claim 7, wherein the ligand is $P(R^5)(R^6)(R^7)$ or $(R^5)(R^6)P-(Y)-P(R^5)(R^6)$ wherein $R^5$, $R^6$ and $R^7$ each independently are $C_{1-8}$-alkyl, cyclohexyl, benzyl, naphthyl, 2- or 3-pyrrolyl, 2- or 3-furyl, 2- or 3-thiophenyl, 2- or 3- or 4-pyridyl, phenyl or phenyl which is substituted by $C_{1-4}$-alkyl, $C_{1-4}$-alkoxy, halogen, trifluoromethyl, lower alkylydenedioxy or phenyl and Y is binaphthyl, 6,6'-dimethyl- or 6,6'-dimethoxybiphenyl-2,2'-diyl, or one of the groups $-(CH_2)_n-$, $-CH_2CH_2-P(C_6H_5)-CH_2CH_2-$,

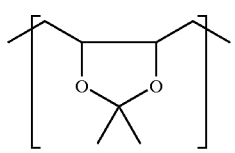 or 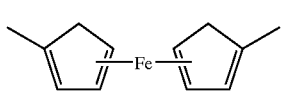  (IV)

and n is a number of 1–8.

13. The process according to claim 12, wherein the ligand is selected from the group consisting of triphenylphosphine, and

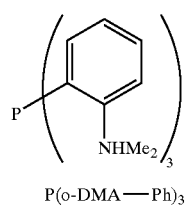 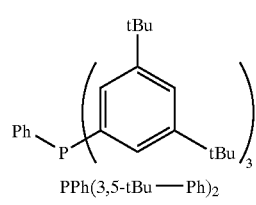

P(o-DMA—Ph)₃      PPh(3,5-tBu—Ph)₂

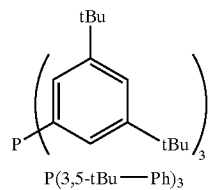 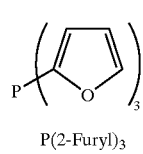

P(3,5-tBu—Ph)₃     P(2-Furyl)₃

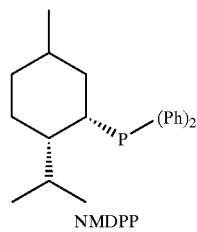 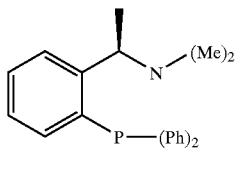

NMDPP             AMPHOS

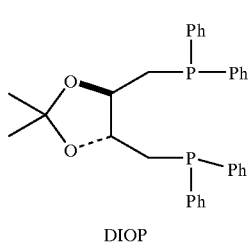 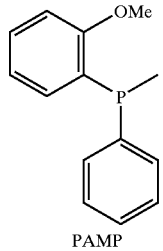

DIOP              PAMP

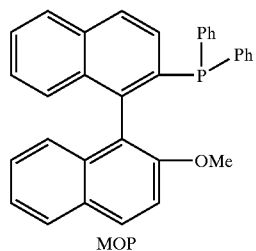 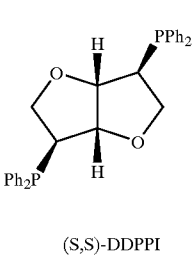

MOP               (S,S)-DDPPI

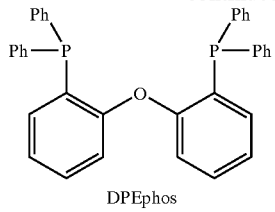 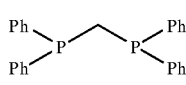

DPEphos           DPPM

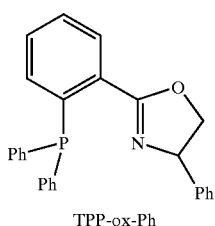 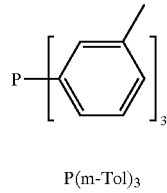

TPP-ox-Ph         P(m-Tol)₃

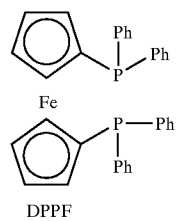

DPPF

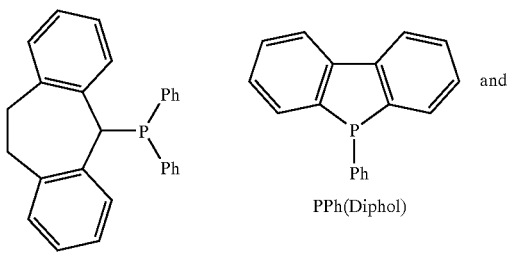 and

TROPP-Ph          PPh(Diphol)

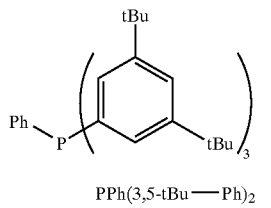 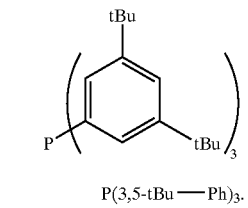

Diphol-DIOP

14. The process according to claim 13, wherein the ligand is triphenylphosphine, PPh(3,5-tBu—Ph)₂  or  P(3,5-tBu—Ph)₃.

15. The process according to claim 8, wherein the ligand is P(R$^5$)(R$^6$)(R$^7$) or (R$^5$)(R$^6$)P—(Y)—P(R$^5$)(R$^6$) wherein R$^5$, R$^6$ and R$^7$ each independently are C$_{1-8}$-alkyl, cyclohexyl, benzyl, naphthyl, 2- or 3-pyrrolyl, 2- or 3-furyl, 2- or 3-thiophenyl, 2- or 3- or 4-pyridyl, phenyl or phenyl which is substituted by C$_{1-4}$-alkyl, C$_{1-4}$-alkoxy, halogen, trifluoromethyl, lower alkylydenedioxy or phenyl and Y is binaphthyl, 6,6'-dimethyl- or 6,6'-dimethoxybiphenyl-2,2'-diyl, or one of the groups —(CH$_2$)$_n$—, —CH$_2$CH$_2$—P(C$_6$H$_5$)—CH$_2$CH$_2$—,

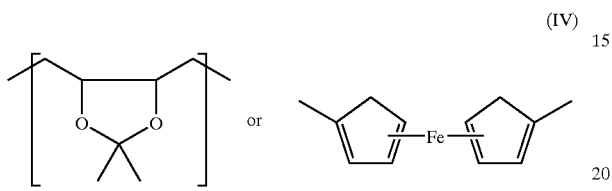

(IV)

and n is a number of 1–8.

16. The process according to claim 15, wherein the ligand is selected from the group consisting of triphenylphosphine, and

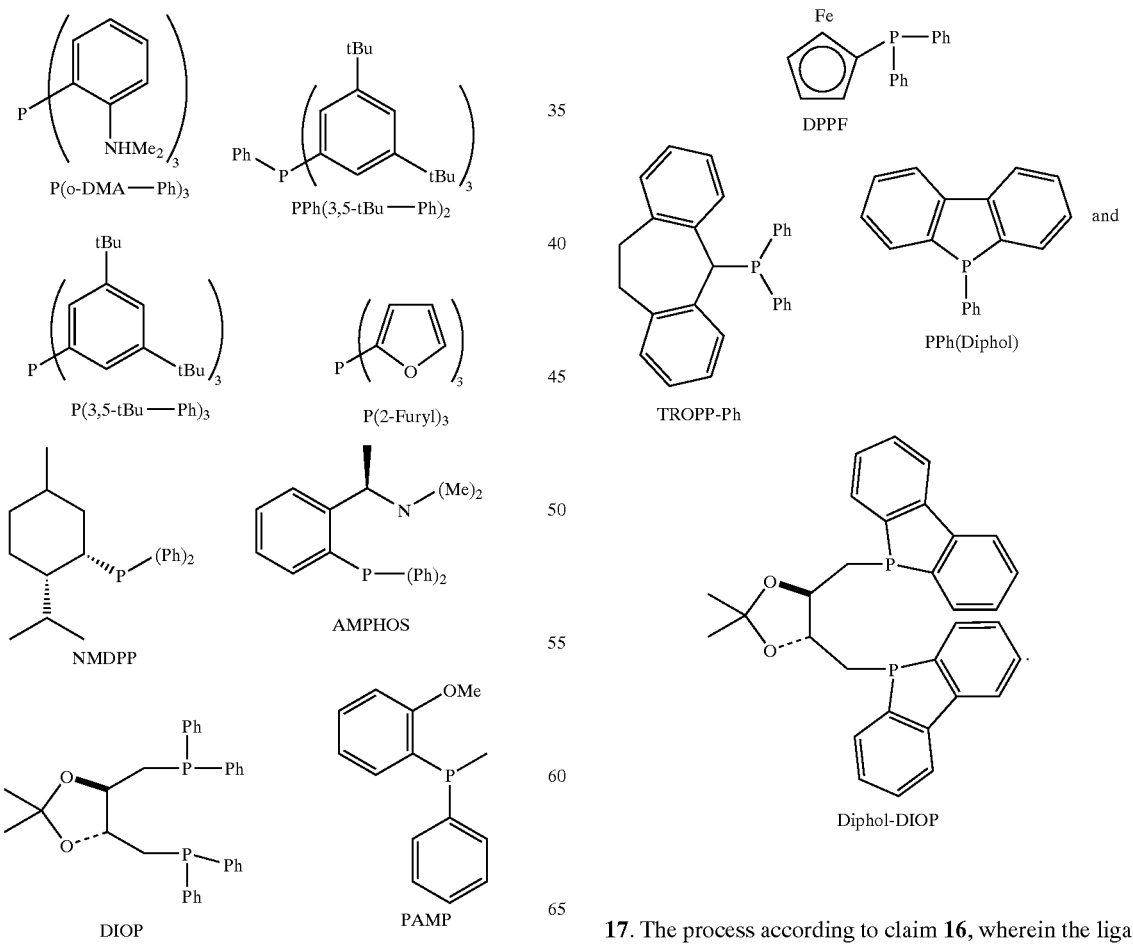

17. The process according to claim 16, wherein the ligand is triphenylphosphine,

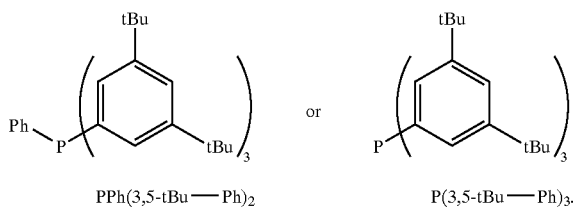

PPh(3,5-tBu—Ph)₂ or P(3,5-tBu—Ph)₃.

18. The process according to claim 5, wherein the cyclocarbonylating is carried out in the presence of a base selected from the group consisting of tri-alkyl-amines, di-alkyl-aryl-amines, pyridines, alkyl-N-piperidines, sodium hydroxide, potassium hydroxide or salts of carbonic acids.

19. The process according to claim 18, wherein the cyclocarbonylating is carried out in the presence of triethylamine.

20. The process according to claim 9, wherein the cyclocarbonylating is carried out in the presence of a base selected from the group consisting of tri-alkyl-amines, di-alkyl-aryl-amines, pyridines, alkyl-N-piperidines, sodium hydroxide, potassium hydroxide or salts of carbonic acids.

21. The process according to claim 20, wherein the cyclocarbonylating is carried out in the presence of triethylamine.

22. The process according to claim 10, wherein the cyclocarbonylating is carried out in the presence of a base selected from the group consisting of tri-alkyl-amines, di-alkyl-aryl-amines, pyridines, alkyl-N-piperidines, sodium hydroxide, potassium hydroxide or salts of carbonic acids.

23. The process according to claim 22, wherein the cyclocarbonylating is carried out in the presence of triethylamine.

24. The process according to claim 11, wherein the cyclocarbonylating is carried out in the presence of a base selected from the group consisting of tri-alkyl-amines, di-alkyl-aryl-amines, pyridines, alkyl-N-piperidines, sodium hydroxide, potassium hydroxide or salts of carbonic acids.

25. The process according to claim 24, wherein the cyclocarbonylating is carried out in the presence of triethylamine.

26. The process according to claim 5, wherein the cyclocarbonylating is carried out in the presence of an anhydride of the formula $(R^4(C=O))_2O$, wherein $R^4$ is as defined in claim 1.

27. The process according to claim 26, wherein the cyclocarbonylating is carried out in the presence of an anhydride selected from acetic anhydride, propionic anhydride, butyric anhydride, isobutyric anhydride, pivalic anhydride and benzoic anhydride.

28. The process according to claim 1, wherein the saponifying is carried out in a biphasic mixture of sodium hydroxide in toluene or in a homogeneous mixture of sodium methylate in methanol.

29. The process according to claim 5, wherein the cyclocarbonylating is carried out in the presence of a base selected from the group consisting of tri-alkyl-amines, di-alkyl-aryl-amines, pyridines, alkyl-N-piperidines, sodium hydroxide, potassium hydroxide and salts of carbonic acids; an anhydride of the formula $(R^4(C=O))_2O$, wherein $R^4$ is as defined in claim 1; and a catalyst comprising a transition metal compound selected from the group consisting of $Pd(OAc)_2$, $Pd_2dba_3$, $PdCl_2$, $Pd_2Cl_2(\square\text{-allyl})_2$, $PdCl_2(NCMe)_2$, $[Pd(NCMe)_4](BF_4)_2$, and Pd/C, and a ligand selected from the group consisting of $P(R^5)(R^6)(R^7)$ and $(R^5)(R^6)P-(Y)-P(R^5)(R^6)$ wherein $R^5$, $R^6$ and $R^7$ each independently are $C_{1-8}$-alkyl, cyclohexyl, benzyl, naphthyl, 2- or 3-pyrrolyl, 2- or 3-furyl, 2- or 3-thiophenyl, 2- or 3- or 4-pyridyl, phenyl or phenyl which is substituted by $C_{1-4}$-alkyl, $C_{1-4}$-alkoxy, halogen, trifluoromethyl, lower alkylydenedioxy or phenyl and Y is binaphthyl, 6,6'-dimethyl- or 6,6'-dimethoxybiphenyl-2,2'-diyl, or one of the groups $-(CH_2)_n-$, $-CH_2CH_2-P(C_6H_5)-CH_2CH_2-$, (IV)

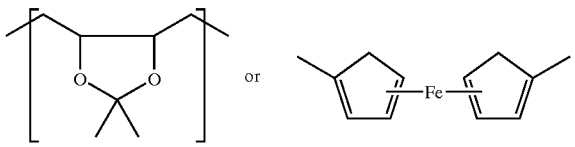

and n is a number of 1–8.

30. The process according to claim 29, wherein the saponifying is carried out in a biphasic mixture of sodium hydroxide in toluene or in a homogeneous mixture of sodium methylate in methanol.

* * * * *